(12) United States Patent
Piskoti et al.

(10) Patent No.: US 8,450,512 B1
(45) Date of Patent: May 28, 2013

(54) AMINOORGANO FUNCTIONAL SILANES AND SILOXANES AND METHODS OF PRODUCTION

(75) Inventors: Charles Piskoti, Burton, MI (US); Charles R. Piskoti, Burton, MI (US)

(73) Assignee: Genesee Polymers Corporation, Burton, MI (US)

( * ) Notice: Subject to any disclaimer, the term of this patent is extended or adjusted under 35 U.S.C. 154(b) by 152 days.

(21) Appl. No.: 12/877,669

(22) Filed: Sep. 8, 2010

Related U.S. Application Data

(60) Provisional application No. 61/240,636, filed on Sep. 8, 2009.

(51) Int. Cl.
*C07F 7/10* (2006.01)

(52) U.S. Cl.
USPC ............................ 556/407; 556/410; 556/411

(58) Field of Classification Search
USPC ...................... 556/407, 411; 427/117; 528/38
See application file for complete search history.

(56) References Cited

U.S. PATENT DOCUMENTS

2004/0077892 A1 * 4/2004 Arkles et al. .................. 556/407

OTHER PUBLICATIONS

Speier J. L. et al; Journal of organic Chemistry; 1971, vol. 36, No. 21.*

* cited by examiner

*Primary Examiner* — Johann Richter
*Assistant Examiner* — Pancham Bakshi
(74) *Attorney, Agent, or Firm* — Young Basile Hanlon & MacFarlane PC

(57) ABSTRACT

Disclosed herein are methods for a simple process to make 3-aminoorgano functional silanes and siloxanes, free from isomers, by the use of commonly available materials. One embodiment of such a method comprises reacting aminoorgano functional silanes with hexamethyldisilazane in the presence of an acidic catalyst to produce a cyclic gamma-functional aminoorganic silane and beta isomers; separating the cyclic gamma-functional aminoorganic silane and the beta isomers; and converting the separated cyclic gamma-functional aminoorganic silane to pure gamma-aminoalkyl-silane or pure aminoorganic siloxane. Also disclosed herein are cyclic derivatives of gamma-functional aminoorganic silanes.

4 Claims, No Drawings

AMINOORGANO FUNCTIONAL SILANES AND SILOXANES AND METHODS OF PRODUCTION

FIELD OF THE INVENTION

The invention relates in general to 3-aminoalkyl end blocked siloxanes and 3-aminoalkyl functional silanes and methods of manufacturing the same.

BACKGROUND

Organosilicon compounds such as amine functional silicones have a wide utility in uses that include, but are not limited to, use in releasing agents, surfactants, copolymers in urethane or epoxy composites, polycarbonates and polyamides. Amine functional silicones also find utility in corrosion resistant coatings and polishes. Present commercial methods for manufacture of these materials suffer from several disadvantages.

Typical manufacture of amine functional silicones involves the reaction of allylamine and silicon-hydrogen functional silanes (or siloxanes) to prepare 3-aminopropyl functional silanes (or siloxanes). These components are coupled by a catalyzed hydrosilation reaction proceeding in the presence of materials such as platinum, rhodium, or other rare earth catalysts. In many cases, prior to the hydrosilation process, the allyl amine nitrogen-hydrogen bonds are partially or completely protected by blocking with trimethylsilyl groups. Upon completion of the hydrosilation step, the material is subjected to a de-blocking step to restore nitrogen-hydrogen bonds.

Many applications call for the use of specific organosilane isomers having the 3-aminopropyl functionality. In certain circumstances, it is the gamma isomer that is desirable, while materials such as the beta isomer are not. In circumstances where the ratio of desirable gamma-aminopropyl to undesirable beta-amino propyl substitution is reported, there is significant beta-isomer present. The presence of beta-isomer can be particularly undesirable in the production of siloxane-modified materials requiring heat stability such as siloxane-modified polyimides.

The respective boiling points for the beta and gamma isomers are quite close. Thus the removal of the beta-isomers of amine alkyl functional monomers (silanes) and disiloxanes has been accomplished through difficult separations by distillation, using complex, multi-plate distillation columns, owing to the very minor difference in boiling points between beta and gamma isomers of aminopropyl adducts. Additionally, the reaction of allyl amine with silicon-hydrogen containing components has been found to produce an impurity resulting from reaction of the amino end group with silicon-hydrogen to yield

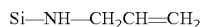

Si—NH—CH$_2$CH=CH$_2$ again impacting the conversion to desired product.

The above considerations have been discussed in U.S. Pat. No. 5,892,084, which states that "[a] simple high-yielding process for producing 3-aminopropylsiloxanes, substantially free of isomeric 2-aminopropylsiloxanes, has clearly been sought for years, to no avail." Further, U.S. Pat. No. 6,087,520 states that "Where is a need to have a method for preparing 1,3-bis(3-aminopropyl)tetramethyl disiloxane of quality in a commercially advantageous manner."

The importance of an improved process for producing 3-aminopropyl functional silanes or siloxanes such as 3-aminoalkyl end blocked siloxanes and 3-aminoalkyl functional silanes can also be appreciated from the discussion in U.S. Pat. No. 5,026,890 where it is observed that "Commercial utilization of these compounds has been inhibited by the lack of convenient methods for their preparation on a large scale."

Thus it would be desirable to provide a method for producing 3-amino-functional silanes and siloxanes such as 3-aminoalkyl end blocked siloxanes and 3-aminoalkyl functional silanes. It would also be desirable to provide a material that is essentially free of isomeric 2 aminopropylsiloxane components.

SUMMARY

Disclosed herein is a method for producing an aminosiloxane compound of the general formula:

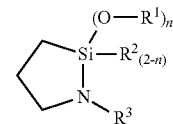

I wherein $R^1$ and $R^2$ are alkyl radicals each having 1 to 18 carbon units, an alkyl-aryl or aryl radicals; and wherein $R^3$ is a an alkyl radical having 1 to 18 carbon atoms, an alkyl-aryl radical, an aryl radical, or trimethylsilyl; and wherein n is an integer equal to 0, 1 or 2.

The method comprises the steps of:

reacting hexamethylsilazane with an aminosiloxane compound of the following general formula:

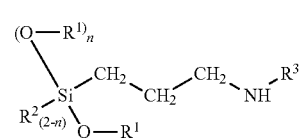

II wherein $R^1$ and $R^2$ are alkyl radicals having 1 to 18 carbon units, an alkyl-aryl or aryl radicals;

wherein $R^3$ is an alkyl radical having 1 to 18 carbon units, an alkyl-aryl radical, an aryl radical or hydrogen and;

wherein n is an integer equal to 0, 1 or 2 to produce an admixture comprising:

a) the compound of general formula I; and b) Me$_3$SiOR$^1$, wherein $R^1$ is an alkyl radical having 1 to 18 carbon units, an alkyl-aryl or an aryl radical.

DETAILED DESCRIPTION

Disclosed herein are methods of producing pure aminoorgano-functional silanes and siloxanes that do not entail the use of allyl amine or substituted allyl amines as a reactive component.

Compounds having the following general formula have specific utility in the preparation of aminoorgansilanes (and siloxane) including, but not limited to, 3-aminoalkyl end-blocked siloxanes and 3-aminoalkyl functional silanes:

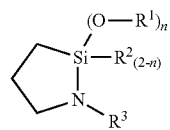

I wherein $R^1$ and $R^2$ are alkyl radicals each having 1 to 18 carbon units, an alkyl-aryl or aryl radicals; and wherein $R^3$ is a an alkyl radical having 1 to 18 carbon atoms, an alkyl-aryl radical, an aryl radical, or trimethylsilyl; and wherein n is an integer equal to 0, 1 or 2.

Compounds of general formula I can be produced according to the process comprising the steps of:

reacting hexamethylsilazane with an aminosiloxane compound of the following general formula:

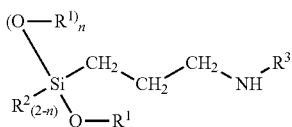

II wherein $R^1$ and $R^2$ are alkyl radicals having 1 to 18 carbon units, an alkyl-aryl or aryl radicals;

wherein $R^3$ is an alkyl radical having 1 to 18 carbon units, an alkyl-aryl radical, an aryl radical or hydrogen and;

wherein n is an integer equal to 0, 1 or 2 to produce an admixture comprising:

a) the compound of general formula I; and b) $Me_3SiOR^1$, wherein $R^1$ is an alkyl radical having 1 to 18 carbon units, an alkyl-aryl or an aryl radical.

In certain specific embodiments, the compound of general formula I will have a trimethylsilyl group as $R^3$ and the aminosilane compound of general formula II is hydrogen. In various embodiments, $R^1$ and $R^2$ can be methyl or ethyl groups, independently.

In various applications $R^3$ can be hydrogen. However trialkylsilyl functionality can be included in situations where additional blockage of the associated nitrogen group is desirable. In such situations, alkyl functionalities having between 1 and 4 carbon atoms, more particularly 1 to 2 carbon atoms, in each alkyl group can be advantageously employed. The materials can be used to produce aminoorganic materials that can be employed to prepare compounds such as 3-aminoalkyl endblocked siloxanes and 3-aminoalkyl functional silanes.

The compound according to formula I can be prepared by reacting suitable aminoorganofunctional silane with hexamethylsilazine in the presence of an acidic catalyst to produce a compound composed of cyclic gamma-functional aminoorganic silane. Broadly construed, the suitable a minoorganofunctional silane material can be one having the general formula:

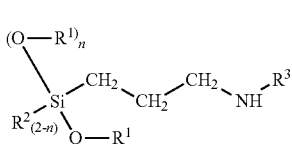

II wherein n is an integer 0, 1, or 2;

wherein $R^1$ and $R^2$ are each independently: alkyl radicals having 1 to 18 carbon units, aryl radicals or alkyl-aryl radicals; and wherein $R^3$ is a alkyl radical having 1 to 18 carbon units, an alkyl-aryl radicals an aryl radical or hydrogen.

The invention disclosed herein is also directed to a composition of matter having the following general formula:

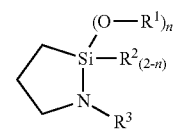

I wherein $R^1$ and $R^2$ are alkyl radicals having 1 to 18 carbon units, an alkyl-aryl or aryl radicals;

wherein $R^3$ is a trimethylsilyl group, and;

wherein n is an integer equal to 0, 1 or 2.

Gamma-functional compounds containing aminoorgano silane material are particularly useful and can be produced by reacting a material containing the compound having the general formula:

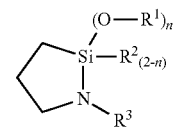

I wherein $R^1$ and $R^2$ are alkyl radicals having 1 to 18 carbon units, alkyl-aryl or aryl radicals;

wherein $R^3$ is an alkyl radical having 1 to 18 carbon units, an alkyl-aryl radical, an aryl radical or a trimethylsilyl; and wherein n is an integer equal to 1 or 2.

This compound is reacted with a suitable reactive compound to produce an intermediate having the general formula:

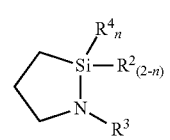

III wherein $R^2$ and $R^4$ are alkyl radicals having 1 to 18 carbon units, alkyl-aryl or aryl radicals;

wherein $R^3$ is an alkyl radical having 1 to 18 carbon units, an alkyl-aryl radical or an aryl radical or a trimethylsilyl; and wherein n is an integer equal to 1 or 2. General formula III is reacted with an excess of a short chain alcohol having the general formula $R^5OH$ to produce a compound having the general formula:

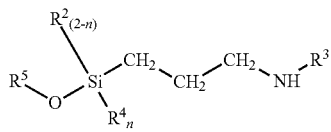

IV wherein $R^2$ and $R^4$ are alkyl radicals having 1 to 18 carbon units, alkyl-aryl or aryl radicals, $R^3$ is hydrogen, an alkyl radical having 1 to 18 carbon units, an alkyl-aryl radical or an aryl radical, $R^5$ is an alkyl radical having 1 to 18 carbon units, an alkyl-aryl radical or an aryl radical; and wherein n is an integer equal to 1 or 2.

In situations where $R^3$ in general formula III is a trimethylsilyl functionality, the reaction will convert $R^3$ to a hydrogen in general formula IV with an associated conversion of trimethylsilyl to a silane of the general formula $(Me)_3SiOR^5$.

The amino silane compound of general formula IV can be reacted with water in the presence of a suitable acid catalyst to produce a compound of the following general formula:

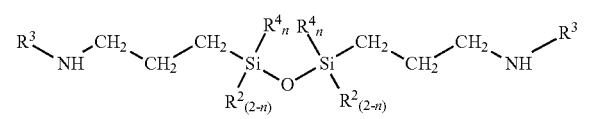

V wherein $R^2$ and $R^4$ are alkyl radicals having 1 to 18 carbon units alkyl-aryl radicals or aryl radicals, and wherein $R^3$ is hydrogen, an alkyl radical having 1 to 18 carbon units, an alkyl-aryl radical or an aryl radical; and wherein n is an integer equal to 1 or 2.

The cyclic amine of general formula I can be synthesized from compositions that contains the pure gamma isomeric form of formula II. The present disclosure also permits and facilitates the use of amino siloxane feedstocks that contain a mixture of the desired gamma isomer and the undesired beta isomer. Disilazanate amines such as hexamethyldisilazane (HMDS, also know as bis(trimethylsilyl)amine) can be employed in the reaction.

The gamma isomer depicted in general formula II preferentially reacts with HDMS in an acid catalyzed reaction to produce the cyclic compound as outlined in General Formula I together with the unreacted beta isomer and $Me_3SiOR^1$. When the isomeric mixture is reacted with a HMDS, the beta isomer remains wholly or essentially wholly unreacted while the gamma isomer is converted into cyclic derivatives of 3-aminooxysilane. The resulting material is a mixture of the cyclic derivative of the gamma isomer in combination with the unreacted beta isomer. The resulting mixture can be further reacted with suitable short chain alcohols ($R^5OH$) to produce material of the general formula:

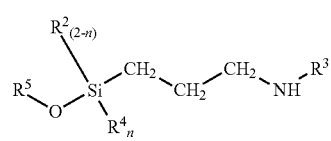

IV

Conversion of the intermediate compound according to general formula I can be accomplished by suitable reaction as by reaction with a Grignard reagent. In such conversion reactions, the Grignard reagent is added to convert the alkoxy group to an R group. Suitable Grignard reagents will have the general formula $R^4MgX$ in which X is a halide and $R^4$ is one of an alkyl, aryl or alkylaryl having 18 carbon atoms or less.

Following the Grignard reagent addition step, the resulting cyclic product can be reacted with a suitable alcohol ($R^5OH$ in which $R^5$ is an alkyl group having 1 to 18 carbon atoms) to produce a silane of general formula IV.

Suitable hydrolytic reaction yields 1,3 bis(3-aminopropyl) teraorganodisiloxane upon removal of the trimethylalkoxysilane as set forth in general formula V:

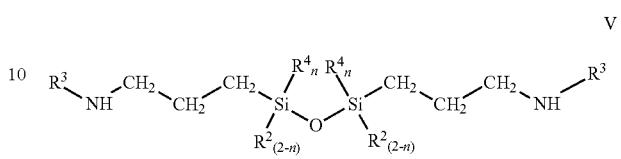

V wherein $R^2$ and $R^4$ are alkyl radicals having 1 to 18 carbon units, alkyl-aryl or aryl radicals, $R^3$ is hydrogen, an alkyl radical having 1 to 18 carbon units, an alkyl-aryl radical or an aryl radical.

The significant amount of trimethylalkoxysilane produced by processes disclosed herein also has significant commercial value. For example trimethylalkoxysilane can be used to synthesize MQ type siloxane resins or as end blocks for siloxane oils.

It is also contemplated that the cyclic reaction product resulting from the addition of the Grignard reagent can alternately be reacted with water to directly convert to 1,3-bis(3-aminopropyl)tetraorganodisiloxane.

Thus production of cyclic gamma-functional aminoorganic silane can be accomplished by reacting impure silane material (containing the gamma isomer and less desired beta isomer) with a material such as hexamethyl disilazane and an acid catalyst to produce a composition that comprises the cyclic derivative of as set forth as general formula I' together with the beta isomer of trimethoxyaminopropyl silane and $Me_3SiOMe$.

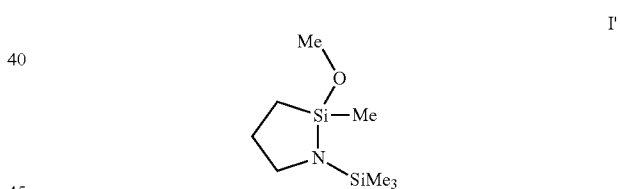

I'

The cyclic derivative can be reacted in admixture with a suitable Grignard reagent to produce an intermediate such as the following:

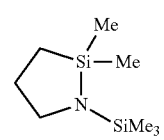

III'

The cyclic gamma-functional aminoorganic silane of general formula III' can be utilized as a material in subsequent reactions as desired or required While the materials depicted result in the production of silanes, it is to be understood that the method disclosed herein can be further employed to produce suitable aminoorgano functional siloxanes where desired or required.

The methods know prior to the present disclosure require the use of highly toxic materials such as allylamines and alkyl amine derivatives in order to produce the desired aminoorgano functional silanes and siloxanes. In processes involving the synthesis of materials such as, 1-3-Bis(3-aminopropyl) tetramethyldisiloxane or other higher molecular weight siloxane analogues, starting materials such as:

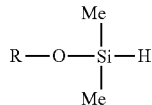

and

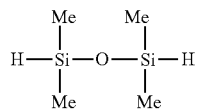

are typically employed. It can be appreciated that these materials can be employed when 1,3-Bis(3-aminopropyl)tetramethyldisiloxane or higher molecular weight siloxane analogues are desired. Typically, these materials are coupled by hydrosilation reactions using platinum, rhodium or other rare earth catalysts. In many cases, the allyl amine nitrogen-hydrogen bonds are protected by blocking with trimethylsilyl groups, either partly or wholly, prior to the hydrosilation process and are then subjected to a de-blocking process step to restore the hydrogen-nitrogen bonds after hydrosilation. The components are difficult to prepare and/or to obtain because of the scarcity of starting materials. Additionally, in examples where the ratio of desired gamma-aminoalkyl material to undesirable beta amino alkyl is reported, there is significant beta-isomer present. The presence of beta-isomer is undesirable in the production of materials such as siloxane-modified polyimides due to impaired heat stability of the resulting material.

Various methods have been proposed for removing undesirable beta-isomers of aminoalkyl functional monomers (silanes) and disiloxanes. Many involve difficult separation processes such as complex multi-plate distillation column processes due to very minor difference in boiling points between beta and gamma isomers of aminopropyl adducts. Also, the reaction of allyl amine with silicon-hydrogen containing components has been found to produce an impurity resulting from reaction of the amine end group with the silicon-hydrogen bond to impact the desired product.

Processes currently employed prior to the present disclosure produce significant amounts of beta-isomers as an impurity along with the desired gamma-isomer of amine end blockers. The methods disclosed herein facilitate elimination of the beta-isomer, resulting in endblocked silicone with much greater advantages in the syntheses of silicone-organic block polymers; a major application of such materials.

Finally, the methods outlined in the present disclosure are much simpler than the other known conventional methods for example, beginning with the addition of allyl chloride and platinum catalyst to the following compound:

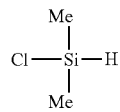

to yield

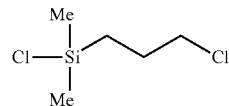

(plus numerous coproducts)

Alcohol addition converts the Si—Cl bond to a Si-alkoxy group. This is followed by reaction with a very large molar excess of ammonia to yield

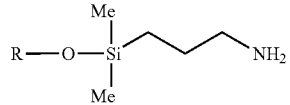

The resulting material can be hydrolyzed to a tetra alkyldisiloxane compound such as 1,3-bis(aminopropyl)tetra methyldisiloxane as depicted:

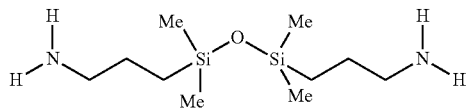 [SMILES: C[Si](C)(CCCN)O[Si](C)(C)CCCN]

The methods disclosed herein also eliminates the need for extremely expensive rare earth catalysts such as platinum or rhodium compounds.

The method and process presently disclosed employ readily obtainable aminoorgano functional silanes as starting materials. Unlike prior methods, the starting materials employed may contain as an impurity their beta isomers. The present method removes the beta isomers, producing pure gamma-functional aminoorgano silanes.

In the disclosed method, impure aminoorgano functional silanes are reacted with hexamethyldisilazane in the presence of acidic catalysts. This reaction converts gamma-functional aminoorgano silanes to a cyclic structure, in which the amine group is blocked by the presence of a trialkylsilyl group in addition to the presence of the amine group in the ring structure. Beta isomers present in the starting material composition do not form a ring structure because of bond angle considerations. The composition that results from the process outlined can contain the ring structure formed from the gamma isomer and linear beta isomeric material. The result is a significant widening of the difference in the respective boiling points of the cyclical gamma derivative (having a lower boiling point) and unreacted beta isomer (having a higher boiling point) relative to the difference between the respective non-cyclical gamma and beta isomers. The relative difference between cyclical gamma derivative and beta isomer facilitates separation. Once recovered, the cyclic gamma isomer can be converted back to pure gamma-aminoorgano silane with the addition of a short chain alcohol, such as methanol if desired One method of producing 3-aminopropyl-substituted silanes and siloxanes, free from isomeric by-products, by the use of commonly available materials will now be described using particular starting materials is outlined in this disclosure. This is presented for purposes of example only without limiting the scope of the disclosed method.

In the first step of the method disclosed herein, a gamma aminoorgano dimethoxysilane such as 3-aminopropylmethyl dimethoxysilane (compound A) in combination with the beta isomer impurity, 2-aminopropylmethyl dimethoxysilane (compound B), is reacted with a material such as hexamethyl disilazane, $Me_3Si—NH—SiMe_3$, in an excess of an acidic catalyst to produce cyclic derivatives of 3-aminopropylmethyl dimethoxysilane (compound C) in combination the compound B impurity, as shown below:

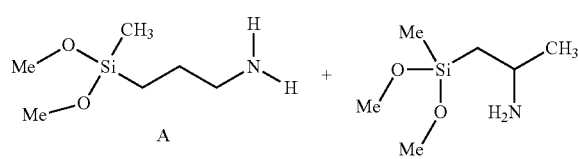

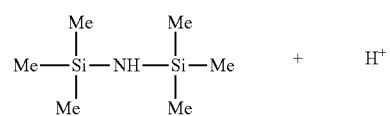

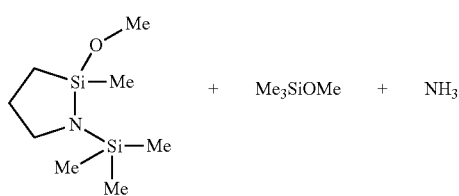

The resulting compound C has a significantly lower boiling point than compound B (approximately 20° C.) allowing for easy separation. Non-limiting examples of suitable separation processes include distillation operations and the like.

As a third step in the multi-step process disclosed herein, compound C can be converted to pure compound (such as general formula I) with no impurity by suitable addition reactions such as by the addition of a short chain alcohol such as adding methanol, as shown below:

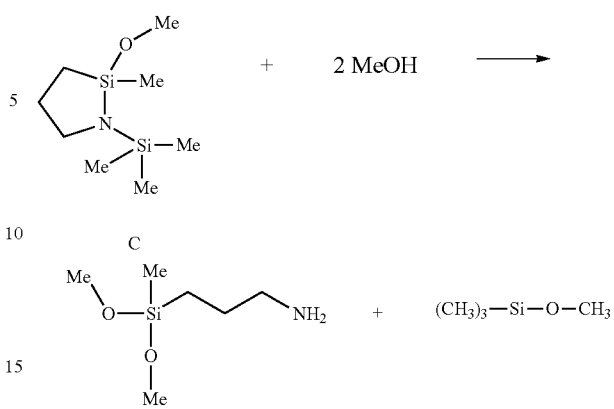

Another commercially important method disclosed herein can be carried out from step two above with the cyclic derivatives of 3-aminoorgano functional silanes (such as the compound at general formula III above) and the use of Grignard reagents. The advantage of the amine cyclic reaction is that the nitrogen is protected from reaction with the Grignard reagent and one site on silicon is preserved for later conversion to an alkoxy —Si functionality or for conversion to a siloxane bond, as described below.

In this method, the gamma-functional silanes are converted to cyclic structures through reaction with hexamethyl disilazane, $Me_3Si—NH—SiMe_3$ in the manner described previously. As in step two above, the resulting cyclic structures are separated from the beta isomer impurities.

The separated cyclic structures are reacted with suitable Grignard Reagent having the general formula RMgX or the like where X is a halogen, and R is an alkyl or aryl (based on a benzene ring) group. By virtue of the cyclic structure, the NH groups present are blocked from reacting with the Grignard reagents facilitating the presentation of one alkoxy radical in the silane.

Reacting the cyclic structures with a suitable Grignard reagent produces the resulting compound IV and MgClOMe salt in the manner depicted as follows:

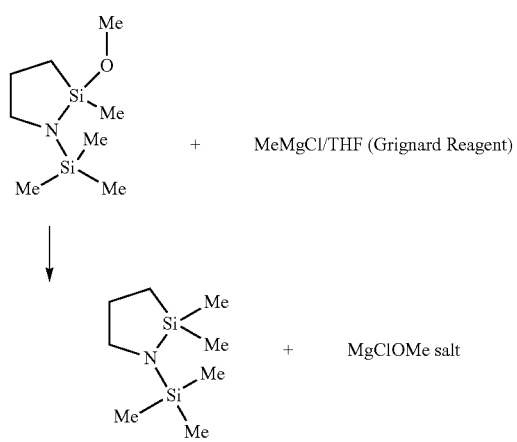

The resulting cyclic compound can be reacted with methyl alcohol in a fourth step to produce a compound according to general formula V and $Me_3SiOMe$ as follows:

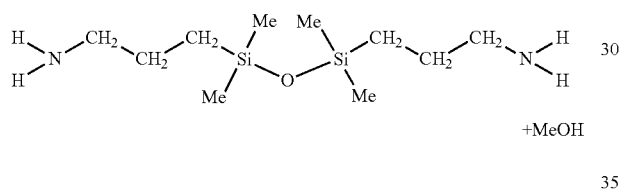

+ 2 MeOH →

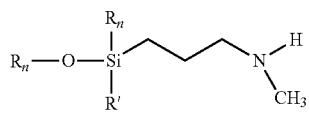 + Me₃SiOMe

The resulting compound can be hydrolyzed to produce a compound according to general formula V, 1,3-bis(3-aminopropyl)tetramethyldisiloxane:

$$\text{H}_2\text{N-CH}_2\text{-CH}_2\text{-CH}_2\text{-Si(Me)}_2\text{-O-Si(Me)}_2\text{-CH}_2\text{-CH}_2\text{-CH}_2\text{-NH}_2$$

+MeOH

Materials such as 1,3-bis(3-aminopropyl)tetramethyldisiloxane, which along with higher molecular weight siloxane analogs, is a highly useful modifier for polyimides and as curing agents for epoxies and polyurethanes.

Reaction with Grignard reagents allows for finished silanes having the following structure:

$$R_n\text{-O-Si}(R_n)(R')\text{-CH}_2\text{CH}_2\text{CH}_2\text{-N(H)(CH}_3\text{)}$$

These materials make valuable end blockers for the synthesis of amine or mercapto endblocked silicone polymers. The process also provides Me₃Si—O—R, wherein R=C₁₋₂ primary or secondary alkyl, phenyl, or substituted phenyl, such as hexamethyldisiloxane (Me₃Si—O—SiMe₃), as a byproduct, which also has significant commercial value.

The methods disclosed herein are conducted in an inert atmosphere. The methods can be conducted at atmospheric pressure; however, the methods can be conducted under other pressure as desired or required by those skilled in the art. The methods can be performed in batches or in a continuous process.

The versatility of the methods described herein can also be shown with N-substituted 3-aminopropylalkoxysilanes, for example N-phenylaminopropyltrimethoxy silane, which is a commercially available amine-silane.

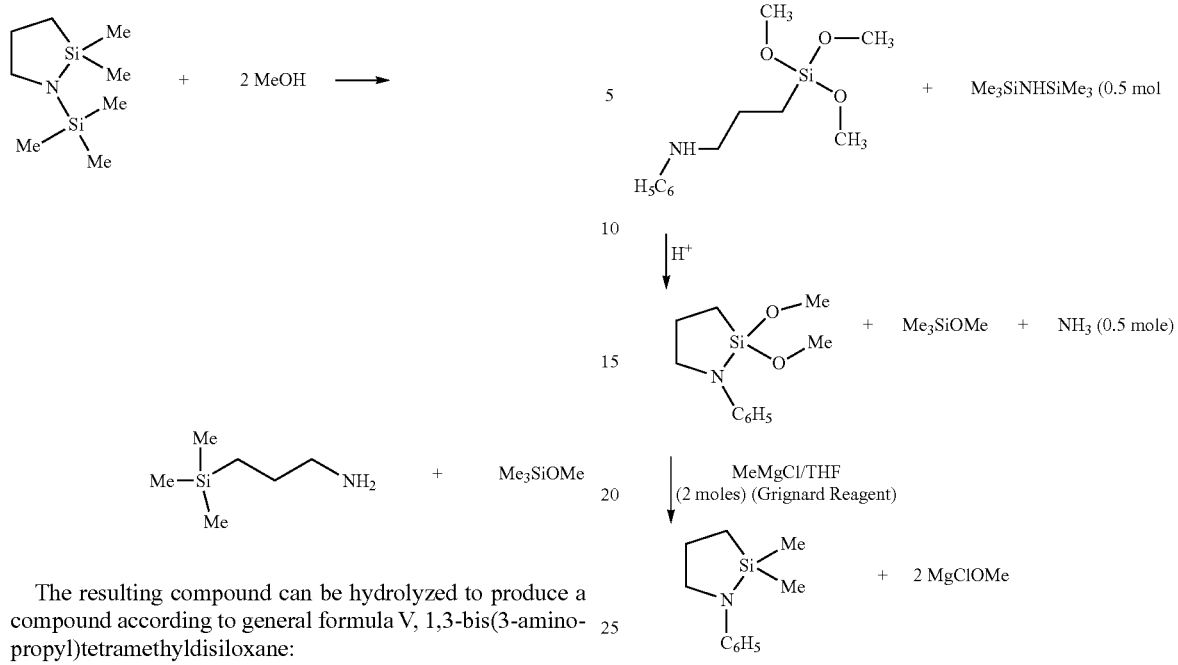

This can be converted to the following silane by MeOH addition:

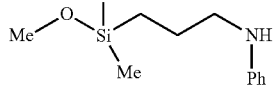

or endblockers based on the following endgroup configuration:

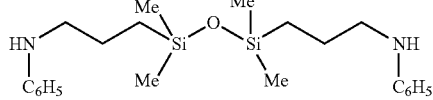

While the invention has been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for producing an aminosiloxane compound the general formula:

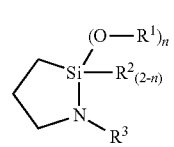

I wherein $R^1$ and $R^2$ are alkyl radicals each having 1 to 18 carbon atoms, an alkyl-aryl or aryl radicals; and wherein $R^3$ is a an alkyl radical having 1 to 18 carbon atoms, an alkyl-aryl radical, an aryl radical, or trimethylsilyl; and wherein n is an integer equal to 0, 1 or 2, the method comprising the step of:

reacting hexamethylsilazane with an aminosiloxane compound of the following general formula:

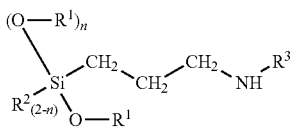

II wherein $R^1$ and $R^2$ are alkyl radicals having 1 to 18 carbon atoms, an alkyl-aryl or aryl radicals;

wherein $R^3$ is an alkyl radical having 1 to 18 carbon units, an alkyl-aryl radical, an aryl radical or hydrogen and;

wherein n is an integer equal to 0, 1 or 2, to produce an admixture comprising:
 a) the compound of general formula I; and
 b) $Me_3SiOR^1$, wherein $R^1$ is an alkyl radical having 1 to 18 carbon atoms, an alkyl-aryl or an aryl radical.

2. The method of claim 1 wherein the compound of general formula I has a trimethylsilyl group as $R^3$ and the compound of general formula II has hydrogen as $R^3$.

3. The method of claim 2 wherein $R^1$ and $R^2$ are both, independently, methyl or ethyl groups.

4. The method of claim 1 wherein the reaction step proceeds in the presence of an acid catalyst.

* * * * *